(12) United States Patent
Krietsch et al.

(10) Patent No.: US 6,227,258 B1
(45) Date of Patent: May 8, 2001

(54) METHOD OF MAKING TEXTILE ARTICLES IMPREGNATED WITH PREDETERMINED LEVELS OF ANTIBACTERIAL ACTIVITY

(76) Inventors: Karl Krietsch; Ronald W. M. Hecht, both of 1745 S. Citation Ave., Tucson, AZ (US) 85713; Paul Denis Samec, 25 Bis Rue des Lazariskes, 01000 Bourg En Bresse (FR)

( * ) Notice: Subject to any disclaimer, the term of this patent is extended or adjusted under 35 U.S.C. 154(b) by 0 days.

(21) Appl. No.: 09/365,395

(22) Filed: Aug. 2, 1999

(51) Int. Cl.⁷ .............................. D03D 15/00; B32B 5/06
(52) U.S. Cl. ...................... 139/420 A; 442/387
(58) Field of Search ............ 442/387; 139/420 A

(56) References Cited

U.S. PATENT DOCUMENTS

| | | | |
|---|---|---|---|
| 4,525,410 | * 6/1985 | Hagiwara et al. | 428/198 |
| 4,775,585 | 10/1988 | Hagiwara et al. | 428/323 |
| 4,826,497 | * 5/1989 | Marcus et al. | 604/359 |
| 5,161,686 | * 11/1992 | Weber et al. | 206/440 |
| 5,652,049 | * 7/1997 | Suzuki | 442/387 |

* cited by examiner

Primary Examiner—John J. Calvert
Assistant Examiner—Robert H. Muromoto, Jr.
(74) Attorney, Agent, or Firm—Antonio R. Durando

(57) ABSTRACT

Empirically determined models allow the predetermination of the accurate amount and quality of modified zeolite required to produce textile articles having a specific degree of antibacterial activity in accordance with the requirements for particular applications. Equations accurately predict the relationship between the amount and spatial orientation of modified-zeolite-containing polymers or fibers and the desired degree of antibacterial activity.

16 Claims, 1 Drawing Sheet

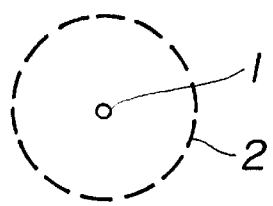
Fig. 1
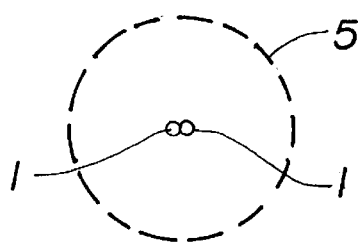
Fig. 2
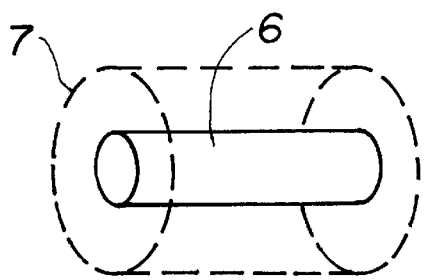
Fig. 3
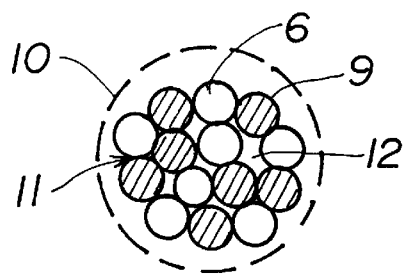
Fig. 4
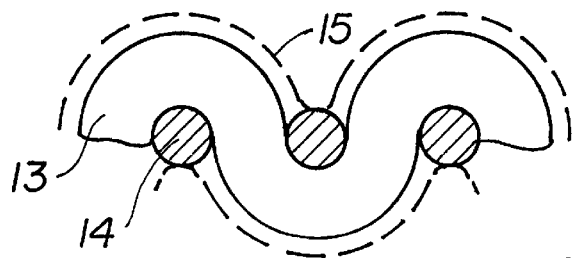
Fig. 5
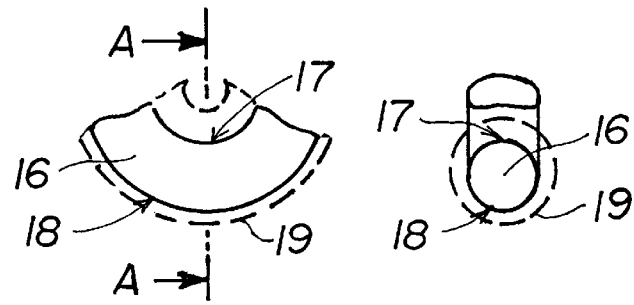
Fig. 6
Fig. 7

METHOD OF MAKING TEXTILE ARTICLES IMPREGNATED WITH PREDETERMINED LEVELS OF ANTIBACTERIAL ACTIVITY

BACKGROUND OF THE INVENTION

1. Field of the Invention

This invention relates in general to the field of textile manufacturing and in particular to a method of making textile articles possessing specific levels of durable antimicrobial activity in accordance with the requirements for particular applications.

2. Description of the Related Art

Textile articles composed of various fibers and/or polymers are used in many applications for which the possession of antibacterial activity would be desirable. For example, such articles and applications may include clothing, fabrics, and linens for use in hospitals, polymer-based materials for use in biomedical research, and woven cloth or metal fibers for use in sanitation or cleaning.

One method of imparting antimicrobial activity to textiles utilizes the addition of antibacterial chemical compounds, such as triclosan. However, one problem with treating textiles with antibacterial chemicals is that such compounds tend to wash out, wear out, or otherwise dissipate after relatively little use.

A means of impregnating a more durable antibacterial activity into textile articles has been accomplished through the addition of a substance known as zeolite. Zeolite is a volcanic rock predominantly made of aluminosilicate which is solvated by calcium and sodium cations. When zeolite is crushed into fine particles and added to a mixture of silver, copper, or zinc salts, the calcium and sodium cations in the aluminosilicate are replaced by silver, copper, or zinc metallic cations to form a compound known as "modified zeolite."

Experiments with modified zeolite demonstrated that the metallic cations, when ionized by the humidity in the surrounding ambient, produce intense electrical fields. These electrical fields lead to the release of oxygen, which has significant antibacterial effects. Furthermore, the metal cations of modified zeolite are capable of chemically mixing with bacterial cell walls, thereby causing growth disruption or destruction of bacterial cells.

It is known that these antibacterial properties can be customized to affect specific microorganisms. Depending on the chemical structure of their cell wall, particular types of bacteria can be disrupted or destroyed according to the metal salt used in the formation of modified zeolite. For example, copper or zinc cations act upon the cell wall of Gram-positive bacteria, whereas silver cations act upon the cell wall of Gram-negative bacteria.

U.S. Pat. No. 4,775,585 by Hagiwara et al. describes a polymer article containing zeolite particles in which a metal ion having bactericidal activity is incorporated in the zeolite by an ion exchange reaction. The polymer article is produced either by admixing metal-ion-containing zeolite particles with a polymer or by molding a zeolite-containing polymer into an article and then treating the article with a metal ion solution. The textile articles made by this method contain between 0.01% and 10% by weight zeolite particles that possess at least one metal ion in an amount less than 92% of the total ion exchange capacity of the zeolite.

However, the antibacterial fiber derived by the method described in the '585 patent has been difficult to exploit in the production of useful articles. Depending on the size and mix of the fibers used, the resulting fabrics have often been unpredictably ineffective or excessively active. For example, a mixture of an apparently adequate percentage of antibacterial fiber with an inert fiber might unexpectedly produce a low-efficacy fabric. Similarly, the resulting fabric might be so active as to destroy all forms of bacteria within its touch, which would render the product unacceptable for use in contact with human skin.

The method of Hagiwara et al. produces textile articles that have undefined levels of antibacterial activity; therefore, they must be tested to determine their level of antibacterial efficacy and the prior art does not provide any teaching for predicting it as a function of textile-design parameters. As will be described hereinafter, the present invention, among other advantages, provides a method of predicting antibacterial properties, thus eliminating the need for efficacy testing of the textile once the properties of the component fibers are known. Nothing has been taught in the prior art to predict the spatial effect of antibacterial fibers and to enable the design of fabrics with a predetermined antibacterial efficacy. The present invention is directed at providing such teachings.

BRIEF SUMMARY OF THE INVENTION

It is an object of the invention to provide a method of making textiles impregnated with a predetermined amount of durable antibacterial material to afford a desired degree of antibacterial activity without the need for laboratory testing of the finished article.

A further object of the invention is to provide a method of making antibacterial textiles possessing specific bacteriostatic levels of antibacterial activity.

Another object of the invention is to provide a method of making antibacterial textiles possessing specific bactericidal levels of antibacterial activity.

Still another object of the invention is to provide a method of making textiles so that they contain the minimum amount of modified zeolite necessary to achieve a desired level of antibacterial activity so as to optimize manufacturing costs.

Moreover, another object of the invention is to provide a method of making antibacterial textiles that contain a minimum of modified zeolite so as to preclude allergenic or otherwise irritating reactions resulting from contact with the skin or mucus membranes.

Yet another object of the invention is to provide a method of making durable antibacterial textiles produced with a maximal amount of non-zeolite-treated natural fibers that are comfortable to wear or touch.

To accomplish these objectives, the invention utilizes novel, empirically determined models that allow the predetermination of the accurate amount and quality of modified zeolite required to produce textile articles having a specific degree of antibacterial activity in accordance with the requirements for particular applications.

One advantage of the present invention is that it minimizes the time and expense of testing newly made textile articles for the presence of bactericidal and/or bacterio-static activity. For this purpose, the invention utilizes equations that accurately predict the relationship between the amount and spatial orientation of modified-zeolite-containing polymers or fibers and the desired degree of antibacterial activity.

Some textiles possess antibacterial activity derived from chemicals that can cause allergy. Moreover, the amount of antimicrobial material that is incorporated into an article, or the chemicals used to affix antimicrobial material to an article, can lead to skin irritation, rashes, or other types of allergenic responses. This is particularly troublesome given the fact that many textiles are worn, held, or are otherwise in bodily contact for long periods of time. Thus, another advantage of the present method is that one can calculate the minimum amount of antimicrobial material necessary to impart a desired level of antibacterial activity, making the textile less irritating or allergenic.

Antibacterial textile articles typically are made from large amounts of modified-zeolite-treated polyester or other synthetic polymers. To provide antibacterial textile articles that are more comfortable, the invention can be utilized to maximize the amount of cotton, silk, and other untreated, natural fibers by determining the minimum amount of modified-zeolite-containing synthetic polymers or fibers necessary to impart a desired antibacterial effect. In so doing, the invention provides for a textile article that is more flexible, breathable, or otherwise tactilely comfortable.

In essence, the invention makes it possible to predict the antibacterial activity of a fabric constructed with a mixture of natural and antibacterial fibers and to design the structure of the fabric such as to ensure that it is antibacterial throughout its surface. This produces a fabric that is entirely and substantially uniformly active according to a predetermined degree of efficacy.

BRIEF DESCRIPTION OF THE DRAWINGS

FIGS. 1 and 2 schematically represent modified particles and their respective spheres of antibacterial influence.

FIG. 3 represents a portion of antibacterial fiber with its cylinder of antibacterial fiber influence.

FIG. 4 represents a section of antibacterial thread with its cylinder of thread influence.

FIG. 5 represents a portion of a section of antibacterial fabric according to the invention.

FIG. 6 represents a portion of antibacterial thread in the shape of a partial torus with its cylinder of thread influence.

FIG. 7 shows a cut-away view of FIG. 6 along line A—A.

DETAILED DESCRIPTION OF THE INVENTION

The invention is based on the idea of providing a model for the antibacterial activity of a fiber or cloth containing a modified zeolite component, This model provides a method of predetermining the antibacterial properties of a textile article based upon the concentration of modified zeolite and the physical parameters of the yarn incorporated in it. Accordingly, the invention enables the prediction of the spatial distribution of antibacterial activity of a textile having predetermined physical characteristics. Moreover, the invention provides a procedure for calculating the minimum amount of modified zeolite needed for a textile product to possess a particular level of antimicrobial activity, thus allowing the production of application-sensitive, non-allergenic textile articles.

As used herein, the term yarn is intended to be inclusive of any thread, filament, fiber, polymer or combinations thereof used in woven textiles. The term denier is a unit of fineness equal to the fineness of a yarn weighing one gram for each 9000 meters. As commonly defined in the art, the term warp refers to a series of yarns extending lengthwise in a loom crossed by the woof or weft, the filling yarn of a woven textile article.

In the description that follows, the textiles are described as made with cotton as a complementary fiber to antibacterial polyester yarn of the type described in U.S. Pat. No. 4,775,585. As would be understood by one skilled in the art, antibacterial polyester yarn can by mixed with other natural or synthetic fibers, either exclusively or in combination, provided that they are of nearly the same denier and length in order to create a mechanically acceptable thread or yarn. It is obvious that the antibacterial thread used in the following description can be replaced by an unlimited number of other synthetic textile fibers, such as polyamide or acrylic resins, that may contain modified zeolite.

The method of the present invention allows the predetermination of the amount and quality of antibacterial fibers containing modified zeolite necessary to produce textiles having a specific antibacterial activity. In general, the method follows from a discovery regarding the way the spatial orientation of the modified-zeolite-treated polymer and/or fiber components of a textile article affects its antimicrobial properties. More specifically, the inventors realized that a particle of modified zeolite has an antibacterial effect not only through direct contact with the particle, but also through a zone of influence within the surrounding volume. In other words, a modified zeolite particle can exert an antibacterial effect over a volume of space that is greater than the volume of the particle itself.

To confirm this discovery, an exemplary textile article was constructed and tested as follows. Modified-zeolite powder was added to a polymer before the polymer was used to make textile fibers as described in U.S. Pat. No. 4,775,585, which is incorporated in its entirety herein by this reference. The polymer, in this case a polyester, was then made into fibers about 38-mm long. These polyester fibers contained a mixture of 50 wt % zeolite modified with silver cations and 50 wt % zeolite modified with copper or zinc cations, totaling 0.8 wt % modified zeolite content overall in the article. The polyester fibers were then mixed with cotton fibers of the same length to form a thread which then could be woven. The polyester used was at least equal to 50 wt % of the mixture with cotton, which corresponds to the minimum level of acceptable antibacterial efficacy shown by load tests. These tests demonstrated that polyester fiber loaded with modified zeolite, hereinafter called "antibacterial fiber," produced an antibacterial effect also on the part of cotton fibers placed close by, even without physical contact.

Based on these findings, the method of the invention was developed to enable the manufacture of woven or non-woven textiles so that the intensity of the antibacterial effect is predetermined based on how modified zeolite is structured within the textile. For example, fabrics can be manufactured such that only parts of the threads composing them contain antibacterial fiber; or non-woven textiles can be manufactured with fibers only parts of which are antibacterial.

Moreover, depending on the application for which the antibacterial textile is intended, it is possible, for example, to produce a bacterio-static effect (halting cell growth) as opposed to a bactericidal effect (destruction of bacteria). In this way, an existing bacterial strain can be preserved or bacterial growth can merely be delayed until the article is removed. This "customization" of a textile article's antimicrobial effect is accomplished by changing the modified zeolite concentration and/or denier of the fibers or polymers used. For example, the modified zeolite concentration in the fabric can be changed by combining the weft thread of a specific denier and constant modified zeolite concentration with a non-zeolite containing warp thread, and by changing the denier of the latter thread to produce the desired result. Consequently, a textile designed according to the method of the invention allows the deduction of its antibacterial properties.

As discussed above, the antibacterial effect of zeolite is due to the presence of silver, copper, or zinc ions (hereinafter "metallic ions"). These metallic ions act directly on bacterial cell walls or indirectly by generating oxygen. Moreover, the volume of antibacterial effect in a given space is in proportion to the density of the above-mentioned metallic ions in the same space. As illustrated in FIG. 1, a modified zeolite particle 1, which may be a few microns in size, is surrounded by a space in which there is antibacterial efficacy. This space is approximated by a sphere 2 within which the metallic ions can affect microorganisms, i.e., the initial sphere of antibacterial influence.

If a second particle 1 of modified zeolite is placed close to the first modified zeolite particle 1 and at a distance less than the radius of their respective spheres 2 of antibacterial influence, both spheres of influence intersect each other and produce an antibacterial space the size of which is greater than the volumes of each separate sphere 2. For example, as seen in FIG. 2, if two modified zeolite particles 1 are placed next to one another in such a way that the spheres of antibacterial influence are concentric, tests have shown that the resulting combined sphere 5 of antibacterial influence will have a diameter approximately 40% greater than the two initial spheres of influence.

By extension, if many particles of modified zeolite are integrated uniformly in an antibacterial fiber 6 as shown in FIG. 3, a volume of antibacterial effect, termed the cylinder 7 of fiber influence, is formed, Thus, a volume of antibacterial protection will be provided by the cylinder 7 of fiber influence that is clearly greater than the volume of the antibacterial fiber 6 itself.

As expected, the diameter of the cylinder 7 of fiber influence varies according to the concentration of modified zeolite in the antibacterial fiber 6. The diameter of the cylinder 7 of fiber influence has not been measured as such, but it has been observed that at least 50% of antibacterial polyester fiber 6 containing 0.8% modified zeolite is needed in a thread in order to obtain a satisfactory antibacterial result, termed "antibacterial effect of reference," as determined by arbitrary, empirical antibacterial tests based on conventional antibacterial-activity standards. For example, a desired antibacterial effect of reference could be the elimination of a certain percentage (e.g., 99%) of a given bacterium (e.g., *Staphylococcus aurus*) after at least one hour of contact with the antibacterial thread.

By further combining multiple fibers into threads, it is understood that the desired effect may be made more intense. As illustrated in FIG. 4, each antibacterial fiber 6 in contact with a cotton fiber 9 of the same length and denier causes an increased cumulative antibacterial effect measured by a cylinder 10 of antimicrobial thread influence. Under these conditions, because of the distribution irregularities of these two types of fiber, it is estimated that the diameter of the cylinder of fiber influence is, at a minimum, 3 to 4 times the diameter of the antibacterial fiber 6; thus, a cotton fiber 9 having the same denier and placed in contact with the antibacterial fiber 6 is contained within the cylinder of fiber influence and acquires an induced antibacterial effect throughout its volume. According to one aspect of the invention, this property of the combined thread is utilized to ensure adequate antibacterial activity throughout the entire surface of the resulting textile.

The following empirical formula was developed to calculate the diameter of the cylinder 7 of antimicrobial fiber influence possessed by an antibacterial fiber 6:

$$DIf = Df\{1 + 2[Cf/(0.8K)]\}^{1/2},$$

where DIf is the diameter of the cylinder 7 of fiber influence; Df is the diameter of the antibacterial fiber 6; Cf is the zeolite concentration in percent by weight of modified zeolite in the antibacterial fiber 6; and K is a correcting coefficient adjusted by calibration on the basis of laboratory tests.

The value of K is selected to be one when the desired antibacterial effect is equal to the "antibacterial effect of reference," as defined above; greater than one for a bactericidal antibacterial effect; and less than one if a bacteriostatic effect is desired. Thus, the invention can also be used to predict the amount of modified zeolite necessary to produce a desired level of antimicrobial activity.

Woven and non-woven textiles, as well as fabrics, can be used in practicing the invention. Cotton fiber may be entirely or partially substituted with other fibers not having an antibacterial effect as long as their use allows manufacture of a thread having appropriate mechanical characteristics. Thus, referring again to FIG. 4, the cylinder 10 of thread influence in a composite thread 11 that contains an average density of modified zeolite is determined by the modified zeolite density in the antibacterial fibers 6 from which it is made and by the proportion of mixed cotton or other fiber 9. For example, a mixture of 50 wt % antibacterial fiber 6 containing 0.8 wt % modified zeolite with 50 wt % cotton fiber 9 has a cylinder 10 of thread influence that corresponds to an average modified zeolite concentration of 0.32 wt %, taking into consideration the free spaces 12 between fibers 6 and 9. These spaces are estimated to result, for example, in an expansion factor (ff) of about 1.25%, which one skilled in the art would recognize to be a realistic and acceptable estimate. If the thread 11 is formed into a yarn containing modified zeolite particles in constant concentration, one can calculate the diameter of the cylinder 10 of thread influence from the diameter of the cylinder 7 of fiber influence of the antibacterial fibers 6 using the following equations:

$$DIF = DF\{(Pf/50)^{1/2} + (DIf/Df - 1)[(CF/Cf)(Df/DF)]^{1/2}\},$$

$$DIf = Df[1 + 2(Cf/0.8K)^{1/2}], \text{ and}$$

$$CF = Cf[Pf/(100ff)0.8],$$

where DIF is the diameter of the cylinder 10 of thread influence; DF is the diameter of the composite thread 11; Df is the diameter of the fiber 6 containing modified zeolite used as the weft; DIf is the diameter of the cylinder 7 of fiber influence; Cf is the modified zeolite concentration in the antibacterial fiber 6 in weight percent; CF is the average modified zeolite concentration in the thread 11 in weight percent; Pf is the weight percentage of antibacterial fiber 6 in the thread 11; and ff is the fiber's expansion factor in the composite thread 11.

Combining the equations above into a single expression, the following equivalent equation is derived:

$$DIF/DF = (Pf/50)^{1/2} + 2[CfPf/(100ffK)*Df/DF]^{1/2}.$$

Thus, to solve for DIF/DF (the diameter of thread influence per thread of a certain diameter), one would first need to determine Df/DF, which is calculated as follows. If one uses warp thread having the metric number of 10, where the metric number 10 is a measure of thread fineness equal to 10 kilometers of thread having a weight of 1 kilogram, then the weight of one kilometer of metric number 10 thread is 100 grams. Assuming the density of this thread is equal to 1, the volume of thread is 100 cm3 and the cross-sectional area (S) of the thread would be $$S=100 \text{ cm3}/100,000 \text{ cm} = 1\times 10^{-3} \text{ cm}^2.$$

Similarly, if one uses weft fiber having a denier of 1.5, where a denier of 1.5 is a measure of fiber fineness equal to 9 kilometers of fiber having a weight of 1.5 grams, then the weight of 1 km of fiber is 1.5/9=0.17 g/km. Assuming the density of this fiber is equal to 1, the volume of the fiber is 0.17 cm3 and the cross-sectional area (s) of the fiber would be $$s=0.17 \text{ cm3}/100,000 \text{ cm} = 1.7\times 10^6 \text{ cm}^2.$$

Since the areas of the thread and fiber above are equal to $\pi r^2$, $$S=(DF/2)^2*3.14 \text{ and } s=(Df/2)^2*3.14.$$

Rearranging, $s/S=(Df/DP)^2$ and $Df/DF=(s/S)^{1/2}$. Thus, $$Df/DF=1.7\times 10^{-6}/1\times 10^{-3}=(0.0017)^{1/2}=0.041.$$

Thus, to determine diameter of thread influence (DIF) for a given diameter of thread (DF) containing 65 wt % antibacterial fiber (Pf=65) and 0.8 wt % modified zeolite (Cf= 0.8), fiber of 1.5 denier, metric number 10 thread, fiber and thread densities approximately equal to 1, an expansion factor (ff) of 1.25, and Df/DF=0.04 as just calculated:

$$DIF/DF=(65/50)^{1/2}+2[(0.8)65/(100)(1.25)*0.04]^{1/2}=1.5,$$

i.e., the calculated diameter of the cylinder of thread influence (DIF) is 1.5 times the diameter of the thread used.

Turning to FIG. 5, an example is given of a warp thread 14 not containing modified zeolite and associated with a weft thread 13 containing modified zeolite. As described, the weft thread 13 creates a sinusoidal cylinder 15 of antimicrobial thread influence that wraps around the warp thread 14, as illustrated in the figure. Consequently, having a weft thread 13 with a known DIF, as calculated with the formula given above, it is possible to estimate the maximum diameter of the warp thread allowable in order to ensure that it is contained within the cylinder of antimicrobial influence of the weft thread, such that the resulting woven fabric is entirely antibacterial. As determined by the geometry of the composite fabric, it is apparent that the theoretical maximum diameter of the warp thread 14 must be between ½(DIF−DF) and (DIF−DF), depending on how tightly woven the warp and weft fibers are.

For example, if one takes a weft thread 13 with a DIF equal to 1.4 DF, the warp thread 14 will be entirely antibacterial if it is tightly woven and its diameter is less than or equal to 0.4 DF. Conversely, if one desires to use a warp thread with a diameter equal to 0.25 DF, one must use a weft thread with a DIF equal to 1.25 DF. If a larger warp thread is desired, it is possible to change the modified zeolite concentration CP in the antibacterial fiber used and/or the antibacterial fiber percentage Pf in the warp thread 13 to produce the equivalent desired result. For example, if a warp thread with a diameter equal to 0.37 DF is used, the calculation based on the above equations, with K=1, indicates that a solution would be to change the percentage of antibacterial fibers to Pf=52%.

The antibacterial weft thread 16 as depicted in FIGS. 6 and 7 shows a shape resembling a torus section with a concave zone 17 and a convex zone 18. In the convex zone 18, a dilution of the metallic ions was discovered, whereas an increase in concentration of metallic ions was seen in the concave zone 17. Thus, the modified thread's volume 19 of influence is no longer concentric with respect to the weft thread 16, but shifts towards the inside of the torus section. Consequently, there is a relatively thick antibacterial zone inside the torus, which protects the warp's thread even better.

In the case of manufacture of non-woven fabric, different types of fibers are mixed with a binding agent, usually a thermoplastic binding material. This mixture is spread in even layers (approximately 100 to 500 grams per square meter) and then compressed and heated to a suitable temperature to allow the fusion of the binding thermoplastic material, thereby ensuring that the fibers hold together and form a non-woven textile sheet. Contrary to woven textiles, the fibers of non-woven textiles are not laid on each other; thus, a much larger expansion factor (FF) of about 12 is normal because the fibers fill only about one-twelfth of the sheet volume. Therefore, an expansion factor FF=12 is used in the following example, although other values are possible.

To create a non-woven antibacterial textile, antibacterial polyester fibers and associated materials are selected according to the desired level of antimicrobial efficacy and other application properties. For example, if one wished to produce a non-woven textile capable of absorbing water for use in cleaning wet surfaces, the fibers would be viscose and the binding thermoplastic material preferably polypropylene. The polypropylene (represented in the equation below by the quantity PP) would be about 15% of the total weight of the sheet. (The space that the sheet occupies is not taken into consideration in the expansion factor because this quantity only relates to the expansion due to the fibers.)

Thus, in the following examples, PP is set at 15 (but other values may apply), based on the assumption that 85 wt % of the non-woven textile sheet weight consists of fiber with FF=12. In order to obtain an antibacterial effect, the antibacterial fibers are introduced spread uniformly and in sufficient quantity for the total sheet volume to be filled by the volumes of the cylinders of fiber influence. The volume of fiber influence (VIf) of a cylinder of fiber influence in such case is expressed as:

$$VIf=(DIf/2)^2 3.14 \text{ L},$$

where L represents the length of the fiber and $DIf=Df[1+2(Cf/0.8K)]^{1/2}$, as defined above.

From a simple geometry, the volume of an antibacterial fiber, designated as "fiber volume" (Vf), is approximately equal to $Vf=(Df/2)^2 3.14 \text{ L}$. Thus, the difference between the volume of fiber influence and the fiber volume, $(VIf-Vf)= [(DIf/2)^2-Df/2]3.14 \text{ L}$, is the volume that can be safely filled, assuming a given expansion factor, by the fibers that do not have an antibacterial effect. The cumulative volume of fibers (VF) located in the fiber influence volume (VIf), which has to be taken into consideration when calculating the respective percentages of antibacterial and non-antibacterial fibers, can be calculated as follows:

$$VF=Vf+(VIf-Vf)/FF,$$

where, for an FF value of 12, one obtains VF=(VIf+11 Vf)/12.

For an average fiber density of one, the reasoning used at the fiber level is also representative of an antibacterial non-woven textile composition, and the results obtained are directly applicable to the whole of the non-woven textile because its composition remains homogenous. One can thus determine the percentage (PF) of antibacterial fibers in the non-woven textile that produces a desired antibacterial effect in the non-woven textile as follows:

$$PF=(Vf/VF)(100-PP),$$

where PP represents the weight percentage of binding thermoplastic material.

For example, if one uses polyester fiber with the specific previous reference content of 0.8 wt % modified-zeolite with a DIf value equal to 3 Df, and if FF=12 and PP=15, a value of PF=51 wt % is obtained (this DIf corresponding to a composition of 51 wt % antibacterial fibers, 15 wt % thermoplastic binding material, and 34 wt % non-antibacterial fibers).

During the weaving process, yarns containing modified zeolite are typically used for weaving of the warp. Compared to the weft, the warp yarn is usually of a much lower denier. In other words, warp containing modified zeolite is much coarser than the weft with which it is woven. Thus, another advantage of the invention is that it allows the manufacture of thin and supple sheets of compact, non-woven fibers ("non-woven textile") as well as more tactilely comfortable woven textile articles.

The process of the invention enables the manufacture of textiles with durable antibacterial efficacy in applications previously deemed unsuitable for the antibacterial fibers developed in the prior art. For example, a mixture of the polyester fiber described above with conventional cotton fiber produced bed sheet material that retained over 80% of its antibacterial activity after 100 wash cycles, which is longer than the normal life of such products.

As would be understood by those skilled in the art, any number of functional equivalents may exist in lieu of the preferred embodiments described above. Thus, as will be apparent to those skilled in the art, changes in the details, steps and materials that have been described may be made within the principles and scope of the invention illustrated herein and defined in the appended claims. Therefore, while the present invention has been shown and described in what is believed to be the most practical and preferred embodiment, it is recognized that departures can be made therefrom within the scope of the invention, which is therefore not to be limited to the details disclosed herein but is to be accorded the full scope of the claims so as to embrace any and all equivalent products and methods.

We claim:

1. A method for manufacturing a textile product having predetermined antibacterial properties, comprising the following steps:
   (a) selecting a fiber containing an antibacterial agent;
   (b) determining an antibacterial effect of reference for said fiber;
   (c) determining a volume of antibacterial influence within which the fiber produces an antibacterial effect corresponding to said antibacterial effect of reference; and
   (d) mixing the fiber with additional components such as to produce a textile product wherein said components are entirely contained within said volume of antibacterial influence;

uniformly distributing modified zeolite as said antibacterial agent with the fiber, admixing said additional components of inert fibers with said fiber containing an antibacterial agent to form a composite thread; step (b) is carried out experimentally; and step (c) is carried out using the following equation:

$$DIF/DF=(Pf/50)^{1/2}+2[CfPf/(100 f\!f\!K)(Df/DF)]^{1/2},$$

where DIF is a diameter of a cylinder of antibacterial influence for the thread; DF is a diameter of the thread; Df is a diameter of the fiber containing modified zeolite used as a weft; DIf is a diameter of a cylinder of antibacterial influence for the fiber; Df is a diameter of the fiber; Cf is a concentration of the modified zeolite in the fiber in percent by weight; Pf is a percentage by weight of fiber in the thread; ff is an expansion factor of the fiber in the thread; and K is an empirical coefficient selected to be one if an antibacterial effect equal to the antibacterial effect of reference is desired, greater than one if a bactericidal effect is desired, and less than one if a bacterio-static effect is desired.

2. A method for manufacturing a textile product having predetermined antibacterial properties, comprising the following steps:
   (a) selecting a fiber containing an antibacterial agent:
   (b) determining an antibacterial effect of reference for said fiber;
   (c) determining a volume of antibacterial influence within which the fiber produces an antibacterial effect corresponding to said antibacterial effect of reference; and
   (d) mixing the fiber with additional components such as to produce a textile product wherein said components are entirely contained within said volume of antibacterial influence,
   wherein said antibacterial agent is uniformly distributed within the fiber; the antibacterial agent is modified zeolite; step (b) is carried out experimentally; and step (c) is carried out using the following equation:

$$DIf=Df\{1+2[Cf/(0.8K)]\}^{1/2},$$

where DIf is a diameter of a cylinder of antibacterial influence for the fiber; Df is a diameter of the fiber; Cf is a concentration of the modified zeolite in the fiber in percent by weight; and K is an empirical coefficient selected to be one if an antibacterial effect equal to the antibacterial effect of reference is desired, greater than one if a bactericidal effect is desired, and less than one if a bacterio-static effect is desired.

3. The method of claim 1, wherein said textile product is woven.

4. The method of claim 2, wherein said textile product is woven.

5. A method for manufacturing a textile product having predetermined antibacterial properties, comprising the following steps:
   (a) selecting a fiber containing an antibacterial agent;
   (b) determining an antibacterial effect of reference for said fiber;
   (c) determining a volume of antibacterial influence within which the fiber produces an antibacterial effect corresponding to said antibacterial effect of reference;
   (d) mixing the fiber with additional components such as to produce a textile product wherein said components are entirely contained within said volume of antibacterial influence;

wherein said textile product is woven; said antibacterial agent is uniformly distributed within the fiber; step (b) is carried out experimentally; and wherein the antibacterial agent is modified zeolite, said additional components are used in a warp thread having a predetermined warp-thread diameter, said fiber is used in a weft thread having a predetermined weft-thread diameter, said weft thread has a cylinder of antibacterial influence having a predetermined antibacterial-influence diameter, and said warp-thread diameter is not greater than a difference between said antibacterial-influence diameter and said weft-thread diameter.

6. The method of claim 1, wherein said textile product is non-woven.

7. The method of claim 2, wherein said textile product is non-woven.

8. A method for manufacturing a textile product having predetermined antibacterial properties, comprising the following steps:

(a) selecting a fiber containing an antibacterial agent;

(b) determining antibacterial effect of reference for said fiber;

(c) determining a volume of antibacterial influence within which the fiber produces an antibacterial effect corresponding to said antibacterial effect of reference; and (d) mixing the fiber with additional components such as to produce a textile product wherein said components are entirely contained within said volume of antibacterial influence;

wherein said textile product is non-woven, the antibacterial agent is modified zeolite uniformly distributed within the fiber, said additional components comprise thermoplastic material, step (b) is carried out experimentally, and step (c) is carried out using the following equation:

$$DIf = Df\{1 + 2[Cf/(0.8K)]\}^{1/2},$$

where DIf is a diameter of a cylinder of antibacterial influence for the fiber; Df is a diameter of the fiber; Cf is a concentration of the modified zeolite in the fiber in percent by weight; and K is an empirical coefficient selected to be one if an antibacterial effect equal to the antibacterial effect of reference is desired, greater than one if a bactericidal effect is desired, and less than one if a bacterio-static effect is desired; and wherein a cumulative volume available for additional components in said volume of antibacterial influence is calculated using the following equation:

$$VF = Vf + (VIf - Vf)/FF,$$

where, VF is said cumulative volume of additional components; Vf is a volume of antibacterial fiber; and VIF a volume of fiber influence of the antibacterial fiber.

9. A textile product manufactured according to the method of claim 3.

10. A textile product manufactured according to the method of claim 4.

11. The method of claim 5, wherein said textile product is woven.

12. The method of claim 8, wherein said textile product is woven.

13. A textile product manufactured according to the method of claim 11.

14. The method of claim 5, wherein said textile product is non-woven.

15. A textile product manufactured according to the method of claim 12.

16. The method of claim 8, wherein said textile product is non-woven.

\* \* \* \* \*